United States Patent
Gilder et al.

(10) Patent No.: US 7,985,468 B1
(45) Date of Patent: Jul. 26, 2011

(54) FOAM EAR PLUG OR EARPIECE UTILIZING RECYCLED PULVERIZED POLYURETHANE FOAM

(75) Inventors: Stephen D. Gilder, Chula Vista, CA (US); Jim Tiemens, Laguna Niguel, CA (US); Larry Sanders, Chula Vista, CA (US)

(73) Assignee: Sperian Hearing Protection, LLC, San Diego, CA (US)

( * ) Notice: Subject to any disclaimer, the term of this patent is extended or adjusted under 35 U.S.C. 154(b) by 534 days.

(21) Appl. No.: 12/182,930

(22) Filed: Jul. 30, 2008

Related U.S. Application Data

(60) Provisional application No. 60/962,593, filed on Jul. 30, 2007.

(51) Int. Cl.
*B32B 5/20* (2006.01)
*B29C 44/34* (2006.01)
*C08L 75/04* (2006.01)

(52) U.S. Cl. .................. 428/317.9; 264/51; 264/331.19; 521/137; 521/170

(58) Field of Classification Search ............... 428/317.9; 264/51, 331.19; 521/137, 170
See application file for complete search history.

(56) References Cited

U.S. PATENT DOCUMENTS

| | | | | |
|---|---|---|---|---|
| 4,438,221 A | * | 3/1984 | Fracalossi et al. | 521/55 |
| 4,855,052 A | * | 8/1989 | Reischl | 210/632 |

* cited by examiner

*Primary Examiner* — Hai Vo
(74) *Attorney, Agent, or Firm* — Timothy Thut Tyson; Norton R. Townsley Freilich, Hornbaker & Rosen

(57) ABSTRACT

An earpiece of flexible foam construction which incorporates recycled pulverized polyurethane foam (RPPF). RPPF constituting 5% to 30% of the improved foam has been found to be useful. The novel and unique nature of RPPF allows for the replacement of a higher cost component with a lower cost component while maintaining or improving physical properties, such as sound attenuation, sound control, comfort and fit.

6 Claims, No Drawings

FOAM EAR PLUG OR EARPIECE UTILIZING RECYCLED PULVERIZED POLYURETHANE FOAM

CROSS REFERENCE TO RELATED APPLICATIONS

The Applicants claim the benefit of their Provisional Application Ser. No. 60/962,593, filed Jul. 30, 2007. In addition, the following U.S. Patents and U.S. Patent Application Publications are included herein by reference in their entireties:

| Number | Title |
| --- | --- |
| 4,774,938 | Slow recovery earplug with largely impenetrable surface |
| 6,670,404 | Polymeric foam powder processing techniques, foam powders products, and foams produced containing those foam powders |
| 6,994,464 | Control system and method for continuous mixing of slurry with removal of entrained bubbles |
| 7,029,162 | Process and apparatus for continuous mixing of slurry with removal of entrained bubbles |
| 2003/0227817 | Mixer |
| 2003/0227818 | Process and apparatus for continuous mixing of slurry with removal of entrained bubbles |
| 2003/0227819 | Control system and method for continuous mixing of slurry with removal of entrained bubbles |
| 2003/0233937 | Apparatus and method for continuously removing air from a mixture of ground polyurethane particles and a polyol liquid |
| 2004/0020540 | Surge tank |
| 2004/0112996 | Process for pulverization of polyurethane-containing materials |
| 2004/0171707 | Polymeric foam powder processing techniques, foam powders products, and foams produced containing those foam powders |
| 2005/0096399 | Method for recycling polyurethane and a composition comprising recycled polyurethane |
| 2005/0096400 | Method for recycling polyurethane and a composition comprising recycled polyurethane |
| 2005/0209354 | Polymeric foam powder processing techniques, foam powders products, and foams produced containing those foam powders |
| 2005/0237853 | Mixer |
| 2006/0104156 | Process and apparatus for continuous mixing of slurry with removal of entrained bubbles |
| 2007/0155843 | Polymeric foam powder processing techniques, foam powders products, and foam produced containing those foam powders |

BACKGROUND OF THE INVENTION (1) Field of the Invention

The present invention relates to the field of earpieces (such as earplugs, ear phones, and earbuds) and more particularly to earpieces made of polyurethane foam.

(2) Description of the Related Art

Earpieces are earplugs that fit into the ear canal, with the function of protecting the user from unwanted external noise. Earpieces may also be earplugs with a sound passageway through the acoustic seal that fit into the user's ear canal. Earpieces are part of a larger group of headpieces that fit in, on, or around the ear. Headpieces (including earpieces, earbuds and stereo pieces) are pairs of small speakers, or less commonly single speakers, with ways of holding them close to or in a user's ears, and with a means of connecting them to a sound source such as an audio amplifier, radio, CD player, MP3 player, or any other communications or sound-modifying device. They can consist of any audio or sound device or component that attenuates, transmits or modifies sound and that is designed to be used in, on, or around the ear. Although earpieces can be made from a variety of materials, the vast majority of earplugs and a growing number of other earpieces are made of polyurethane foam. Such foam is comfortable, non-toxic, manufacturing-friendly and highly effective as a sound-attenuation material, providing the user with a good fit and acoustic seal, as required.

Current art for the production of molded flexible polyurethane foams consist of mixing isocyanates (A-side) with isocyanate-reactive hydrogen-containing compounds (B-side) in the presence of a foaming agent such as water or carbon dioxide. The resulting exothermic reaction produces flexible polyurethane foam.

Prior to reaction, the A-side (isocyanates) and the B-side (hydrogen-containing compounds) are mixed and the resulting blend is able to flow. At this stage the mixture is usually dispensed into the cavity of a mold. The chemicals react and expand into foam and fill the cavity of the mold. The mold can be an open mold, a closed mold, or a reaction-injection mold. For maximum process stability the exothermic reaction best proceeds under controlled temperature conditions. Chemical reaction speeds and foam physical properties can also be altered through the use of a wide variety of catalysts and additives. Such additives may include: surfactants, catalysts, chain-extenders, cross-linkers, pH modifiers, blowing agents, inorganic and organic fillers, coefficient-of-friction modifiers, anti-microbial agents, mineral oil, vegetable oil, and others.

A special polyurethane foam for making earpieces has been developed by Sperian Hearing Protection, LLC. The A-side component of the formulation consists of a prepolymer. The B-side is a hydrogen-providing compound, along with other property-modifying agents that when reacted together produce a slow-recovery polyurethane foam at low cost. This special formulation is used to make earpieces consistent with those described in the previous U.S. Pat. No. 4,774,938.

Foam formulators are always searching for ways to manufacture foams at low cost. While the use of recycled material is common in other plastics, especially thermoplastics, the use of recycled pulverized polyurethane foam (RPPF) has not, to date, been successful in the manufacture of earpieces. The reasons for this include:

difficulty in keeping the pulverized foam in suspension;

difficulties with pumping, mixing and metering a blend containing particles;

incompatibility of the recycled foam with the polyurethane foam made;

difficulty in integrating the RPPF into the polymer matrix;

uncleanliness of the recycled foam; and, inability to maintain critical properties such as: attenuation, comfort, strength, recovery time, density, particle dispersion, impression force depression, reaction time, skin formation, rise time, cream time, coefficient of friction, cell size, strut and window configuration in cell walls, open and closed cell distribution, colorant absorption, color fastness, flame resistance, u.v. inhibition, and antioxidant properties.

Development of a method for making polyurethane foam earpieces more inexpensively by incorporating recycled foam into the formulation represents a great improvement in the field of earpieces manufacture and satisfies a long-felt need of the earpiece manufacturer.

SUMMARY OF THE INVENTION

The present invention is an earpiece of flexible foam construction in which the material is enhanced by the addition of recycled pulverized polyurethane foam (RPPF) in the base formula. The novel and unique nature of RPPF allows for the replacement of a higher cost component with a lower cost component while maintaining or improving physical properties; such as sound attenuation, sound control, comfort and fit.

Recent improvements in reclamation technologies have made it possible to recycle polyurethane foam. The recycled foam may be conventional, high-resilient, visco-elastic, or other types but it must be clean. The resulting polyurethane foam containing recycled components yields flexible polyurethane foam earpieces that cost significantly less than ones molded from conventional foam but that still meet all necessary requirements.

This invention is an improved polyurethane foam earpiece in which the improvement comprises a percentage of recycled pulverized polyurethane foam incorporated in the improved polyurethane foam. A percentage varying from 5 to 30% has been found to be useful. Earpieces made from the improved polyurethane foam have the same attenuation, dimensions, weight, and recovery time as earpieces made from standard polyurethane foam. They conform to the shape of the ear canal and provide a seal as well as earpieces made from standard polyurethane foam.

This invention is also an improved method of making polyurethane foam for earpieces in which the improvement comprises the steps of mixing a percentage of recycled pulverized polyurethane foam (RPPF) into the B-side (hydrogen-containing compounds) component formula and achieving a uniform suspension. The resulting blend is then mixed with the A-side (isocyanates), poured into molds, foamed and cured.

Thus the method comprises the steps of:

mixing a quantity of RPPF and a measured quantity of the B-side formula;

blending to produce an improve B-side blend having a uniform suspension;

mixing the improved B-side blend with the A-side isocyanate component to produce an improved slow-recovery polyurethane foam mix; and, using the improved polyurethane foam mix to fabricate earpieces.

Percentages varying from 5 to 30% have been found achievable. Blending is performed to achieve uniform dispersion and suspension. Fabricating is preferably done on an earpiece molding machine in which the improved polyurethane foam mix is metered into an earpiece mold and the improved polyurethane foam mix is then allowed to foam and cure inside the mold. The improved polyurethane foam mix processes the same as the regular polyurethane foam mix and has no adverse effects on the equipment.

An appreciation of the other aims and objectives of the present invention and an understanding of it may be achieved by referring to the following description of a preferred embodiment.

DETAILED DESCRIPTION OF THE PREFERRED EMBODIMENT

While the present invention is described herein with reference to illustrative embodiments for particular applications, it should be understood that the invention is not limited thereto. Those having ordinary skill in the art and having access to the teachings provided herein will recognize additional modifications, applications, and embodiments within the scope thereof and additional fields in which the present invention would be of significant utility.

Mobius Technologies of Grass Valley, Calif., has developed a process for recycling foam. The process can be applied to any polyurethane feedstock, including the following: slab stock foam (e.g, conventional, high resiliency and visco-elastic), molded foam (e.g., car seats), rigid foam (e.g., insulation panels, refrigerator foam), and semi-rigid foam (e.g., headliner scrap).

The process comprises several steps. In the first step the foam scrap is shredded to pieces about the size of popcorn. In the next step the shredded pieces are reduced in a roll mill to an ultra fine powder. Finally the powder is passed through a proprietary sifter in which coarse particles are separated for recycling back to the roll mill. it has been found that the particle size of the recycled foam powder varies from 53 to 212 microns. The process of making the recycled polyurethane foam powder is covered by one or more of the following U.S. Patents and U.S. Patent Application Publications:

| Number | Title |
| --- | --- |
| 6,670,404 | Polymeric foam powder processing techniques, foam powders products, and foams produced containing those foam powders |
| 6,994,464 | Control system and method for continuous mixing of slurry with removal of entrained bubbles |
| 7,029,162 | Process and apparatus for continuous mixing of slurry with removal of entrained bubbles |
| 2003/0227817 | Mixer |
| 2003/0227818 | Process and apparatus for continuous mixing of slurry with removal of entrained bubbles |
| 2003/0227819 | Control system and method for continuous mixing of slurry with removal of entrained bubbles |
| 2003/0233937 | Apparatus and method for continuously removing air from a mixture of ground polyurethane particles and a polyol liquid |
| 2004/0020540 | Surge tank |
| 2004/0112996 | Process for pulverization of polyurethane-containing materials |
| 2004/0171707 | Polymeric foam powder processing techniques, foam powders products, and foams produced containing those foam powders |
| 2005/0096399 | Method for recycling polyurethane and a composition comprising recycled polyurethane |
| 2005/0096400 | Method for recycling polyurethane and a composition comprising recycled polyurethane |
| 2005/0209354 | Polymeric foam powder processing techniques, foam powders products, and foams produced containing those foam powders |
| 2005/0237853 | Mixer |
| 2006/0104156 | Process and apparatus for continuous mixing of slurry with removal of entrained bubbles |
| 2007/0155843 | Polymeric foam powder processing techniques, foam powders products, and foam produced containing those foam powders |

Earpieces are industry rated and labeled according to the Noise Reduction Rating (NRR) that they achieve. NRR is a number calculated from attenuation data as measured in human subjects. Artificial ear testing is also a useful means of gaining preliminary data of the effectiveness of attenuation properties of earpieces.

It has been found that substitutions of RPPF between 5% and 30% by weight of the active ingredients in polyurethane foam for making, earbuds have yielded successful results. Testing of polyurethane foam including recycled foam shows that there are no adverse affects to attenuation, dimensions, weight, and recovery time with additions of recycled foam at these levels.

In addition to the cost savings provided by use of RPPF, other advantages include: optimizing cell size, additional nucleating sites for bubble formation, smoother skin, and other desirable physical properties.

A further advantage is the elimination of or supplementing of the use of inorganic fillers such as barium sulfate and calcium carbonate with organic fillers such as starch and others, thereby improving the biodegradability and recyclability of the product.

An additional benefit may result from being able to reduce the proportion of the A-side material, so that the higher-cost isocyanate component can be reduced relative to the lower-cost B-side.

The recycled pulverized polyurethane foam can also be used along with other additives to control cell structure and degree of open-closed cells. Other compatible additives can include: surfactants, UV stabilizers, chain extenders, blowing agents, cross-linkers, co-efficient of friction modifiers, mineral oil, vegetable oil, and others.

EXAMPLE

Test batches of polyurethane formulations were mixed with substitutions of 10 and 20% by weight of recycled foam powder. Prior to mixing the B-side portion of the special polyurethane formulation, the standard blend consists of 60% solids and 40% water.

The desired percentages of recycled pulverized polyurethane foam were added to the B-side formula, with care taken to maintain the required viscosity range. Then the test B-side blend was processed in an earbud molding machine. As is well known in the industry such machines have automatic metering and processing equipment for mixing the A-side (isocyanates) and the B-side formula and filling the molds. After the molds are filled, the mixture foams and cures.

The test B-side components were processed normally through the machinery with no detrimental effect. The resulting earbuds were tested on an artificial ear to provide initial evaluation of relative attenuation. Testing with the artificial ear showed no significant differences in frequency attenuation curves obtained with earbuds made from the test solutions and earbuds made from the control solutions. In addition, testing showed no differences in roll up, softness, and expansion between the earbuds made from the test formulations and earbuds made from the control formulations.

Thus, the present invention has been described herein with reference to a particular embodiment for a particular application. Those having ordinary skill in the art and access to the present teachings will recognize additional modifications, applications and embodiments within the scope thereof.

It is therefore intended by the appended claims to cover any and all such applications, modifications and embodiments within the scope of the present invention.

What is claimed is:

1. An improved polyurethane foam earpiece in which the improvement comprises: 5 to 30% by weight recycled pulverized polyurethane foam powder incorporated in said improved polyurethane foam; wherein an earpiece made from said improved polyurethane foam has the same sound attenuation, dimensions, weight, and recovery time as an earpiece made from polyurethane foam without said recycled pulverized polyurethane foam powder.

2. A method of making an improved polyurethane foam earpiece comprises the steps of: mixing 5 to 30% by weight recycled pulverized polyurethane foam powder into a B-side hydrogen-providing formula, blending to produce an improved B-side blend, mixing the improved B-side blend with an A-side isocyanate component to produce an improved slow-recovery polyurethane foam mix, molding, foaming and curing to an improved polyurethane foam earpiece; wherein an earpiece made from said improved polyurethane foam has the same sound attenuation, dimensions, weight and recovery time as an earpiece made from slow-recovery polyurethane foam without said recycled pulverized polyurethane foam powder.

3. The method as claimed in claim 2 in which said blending said recycled pulverized polyurethane foam powder and said B-side formula produces an improved B-side blend having a uniform suspension.

4. A method of making an improved polyurethane foam earpiece comprising the steps of:
   a) providing components for a polyurethane foam mix including an A-side isocyanate-containing component and a B-side hydrogen-providing component;
   b) providing recycled pulverized polyurethane foam powder;
   c) mixing 5 to 30% by weight recycled pulverized polyurethane foam powder and a complementary percentage of said B-side component;
   d) blending said recycled pulverized polyurethane foam powder and said B-side component into an improved B-side blend;
   e) mixing said improved B-side blend with said A-side isocyanate component to produce an improved polyurethane foam mix; and,
   f) using said improved polyurethane foam mix to fabricate an earpiece; said earpiece having the same sound attenuation, dimensions, weight, and recovery time as an earpiece made with polyurethane foam mix without said recycled pulverized polyurethane foam powder.

5. The method as claimed in claim 4 in which said blending said recycled pulverized polyurethane foam powder and said B-side component produces a uniform suspension.

6. The method as claimed in claim 4 in which said fabricating step includes the steps of:
   g) metering said improved polyurethane foam mix into an earpiece mold; and,
   h) allowing said improved polyurethane foam mix to foam and cure within said mold; said improved polyurethane foam mix processing the same as polyurethane foam mix without said recycled pulverized polyurethane foam powder and having no adverse effects on equipment.

* * * * *